United States Patent
Artale et al.

(10) Patent No.: US 10,188,450 B2
(45) Date of Patent: *Jan. 29, 2019

(54) BLADE DEPLOYMENT MECHANISMS FOR SURGICAL FORCEPS

(71) Applicant: COVIDIEN LP, Mansfield, MA (US)

(72) Inventors: Ryan C. Artale, Boulder, CO (US); Thomas W. Meiser, Lakewood, CO (US); William J. Dickhans, Longmont, CO (US); Steven E. Butcher, Berthoud, CO (US); Dennis W. Butcher, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 223 days.

This patent is subject to a terminal disclaimer.

(21) Appl. No.: 14/978,854

(22) Filed: Dec. 22, 2015

(65) Prior Publication Data

US 2016/0106496 A1    Apr. 21, 2016

Related U.S. Application Data

(63) Continuation of application No. 14/692,920, filed on Apr. 22, 2015, now Pat. No. 9,381,060, which is a
(Continued)

(51) Int. Cl.
*A61B 17/00* (2006.01)
*A61B 18/14* (2006.01)
(Continued)

(52) U.S. Cl.
CPC ........ *A61B 18/1445* (2013.01); *A61B 17/282* (2013.01); *A61B 17/285* (2013.01);
(Continued)

(58) Field of Classification Search
CPC .................. A61B 17/285; A61B 17/29; A61B 2018/00178; A61B 2018/0063; A61B 2018/1412; A61B 2018/1455
See application file for complete search history.

(56) References Cited

U.S. PATENT DOCUMENTS

| | | |
|---|---|---|
| 3,896,283 A | 7/1975 | Hayden |
| D249,549 S | 9/1978 | Pike |

(Continued)

FOREIGN PATENT DOCUMENTS

| | | |
|---|---|---|
| CN | 101507635 A | 8/2009 |
| DE | 2415263 A1 | 10/1975 |

(Continued)

OTHER PUBLICATIONS

U.S. Appl. No. 12/792,001, filed Jun. 2, 2010.
(Continued)

*Primary Examiner* — Gregory Anderson

(57) ABSTRACT

A forceps includes first and second shafts, each having a jaw member disposed at a distal end thereof. At least one jaw member is moveable from an open to a closed position for grasping tissue therebetween. At least one jaw member is configured for reciprocation of a blade therethrough. A trigger assembly includes a trigger and at least one linkage coupled to the trigger and to the blade such that rotation of the trigger translates the blade between the retracted and the extended position. An interference member moveable between a locked position and an unlocked position is also provided. The interference member is configured to engage the linkage(s) when in the locked position to inhibit translation of the blade from the retracted to the extended position.

19 Claims, 9 Drawing Sheets

Related U.S. Application Data continuation of application No. 12/896,100, filed on Oct. 1, 2010, now Pat. No. 9,017,372.

(51) Int. Cl.
| | |
|---|---|
| *A61B 17/285* | (2006.01) |
| *A61B 17/28* | (2006.01) |
| *A61B 17/128* | (2006.01) |
| *A61B 17/29* | (2006.01) |
| *A61B 17/32* | (2006.01) |
| *A61B 18/00* | (2006.01) |
| *A61B 90/00* | (2016.01) |

(52) U.S. Cl.
CPC ........ *A61B 17/2833* (2013.01); *A61B 17/128* (2013.01); *A61B 17/2812* (2013.01); *A61B 17/2841* (2013.01); *A61B 17/29* (2013.01); *A61B 18/1442* (2013.01); *A61B 2017/320044* (2013.01); *A61B 2017/320052* (2013.01); *A61B 2018/0063* (2013.01); *A61B 2018/0091* (2013.01); *A61B 2018/00178* (2013.01); *A61B 2018/00196* (2013.01); *A61B 2018/146* (2013.01); *A61B 2018/1412* (2013.01); *A61B 2018/1455* (2013.01); *A61B 2090/08021* (2016.02)

(56) References Cited

U.S. PATENT DOCUMENTS

| | | |
|---|---|---|
| D263,020 S | 2/1982 | Rau, III |
| 4,659,881 A | 4/1987 | Dowe |
| 4,661,667 A | 4/1987 | Sorimachi et al. |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,931,047 A | 6/1990 | Broadwin et al. |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,403,312 A | 4/1995 | Yates et al. |
| D358,887 S | 5/1995 | Feinberg |
| 5,510,584 A | 4/1996 | Norris |
| 5,559,311 A | 9/1996 | Gorbatoff |
| D384,413 S | 9/1997 | Zlock et al. |
| 5,665,100 A | 9/1997 | Yoon |
| 5,717,176 A | 2/1998 | Dahlstrom |
| 5,827,279 A | 10/1998 | Hughett et al. |
| D402,028 S | 12/1998 | Grimm et al. |
| 5,898,147 A | 4/1999 | Domzalski et al. |
| D416,089 S | 11/1999 | Barton et al. |
| D424,694 S | 5/2000 | Tetzlaff et al. |
| D425,201 S | 5/2000 | Tetzlaff et al. |
| 6,270,497 B1 | 8/2001 | Sekino et al. |
| D449,886 S | 10/2001 | Tetzlaff et al. |
| 6,303,887 B1 | 10/2001 | Ando |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| 6,492,602 B2 | 12/2002 | Asai et al. |
| 6,500,169 B1 | 12/2002 | Deng |
| 6,666,875 B1 | 12/2003 | Sakurai et al. |
| 6,673,092 B1 | 1/2004 | Bacher |
| 6,747,218 B2 | 6/2004 | Huseman et al. |
| D493,888 S | 8/2004 | Reschke |
| 6,774,330 B2 | 8/2004 | Blossfeld et al. |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture et al. |
| 7,101,371 B2 | 9/2006 | Dycus et al. |
| D531,311 S | 10/2006 | Guerra et al. |
| 7,131,970 B2 | 11/2006 | Moses et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,244,257 B2 | 7/2007 | Podhajsky et al. |
| 7,252,667 B2 | 8/2007 | Moses et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| 7,811,283 B2 | 10/2010 | Moses et al. |
| 7,837,685 B2 | 11/2010 | Weinberg et al. |
| 7,854,185 B2 | 12/2010 | Zhang et al. |
| 7,896,878 B2 | 3/2011 | Johnson et al. |
| 7,922,718 B2 | 4/2011 | Moses et al. |
| 8,070,748 B2 | 12/2011 | Hixson et al. |
| 8,334,468 B2 | 12/2012 | Palmer et al. |
| 8,338,726 B2 | 12/2012 | Palmer et al. |
| 8,487,199 B2 | 7/2013 | Palmer et al. |
| 8,497,436 B2 | 7/2013 | Palmer et al. |
| 8,497,437 B2 | 7/2013 | Palmer et al. |
| 8,502,091 B2 | 8/2013 | Palmer et al. |
| 8,668,689 B2 | 3/2014 | Dumbauld et al. |
| 8,679,114 B2 | 3/2014 | Chapman et al. |
| 8,696,666 B2 | 4/2014 | Sanai et al. |
| 8,777,945 B2 | 7/2014 | Floume et al. |
| 9,017,372 B2 | 4/2015 | Artale et al. |
| 9,498,245 B2 | 11/2016 | Voegele et al. |
| 9,642,644 B2 | 5/2017 | Houser et al. |
| 2002/0188294 A1 | 12/2002 | Couture et al. |
| 2003/0018332 A1 | 1/2003 | Schmaltz et al. |
| 2003/0199869 A1 | 10/2003 | Johnson et al. |
| 2004/0092927 A1 | 5/2004 | Podhajsky et al. |
| 2005/0107784 A1 | 5/2005 | Moses et al. |
| 2005/0154387 A1* | 7/2005 | Moses ................ A61B 17/2812 606/51 |
| 2006/0074417 A1 | 4/2006 | Cunningham et al. |
| 2006/0100485 A1 | 5/2006 | Arai et al. |
| 2007/0088356 A1 | 4/2007 | Moses et al. |
| 2007/0106297 A1 | 5/2007 | Dumbauld et al. |
| 2007/0246335 A1 | 10/2007 | Sharrah et al. |
| 2008/0004608 A1 | 1/2008 | Dacquay et al. |
| 2008/0164133 A1 | 7/2008 | Hayafune |
| 2008/0167736 A1 | 7/2008 | Swayze et al. |
| 2008/0200940 A1 | 8/2008 | Eichmann et al. |
| 2008/0208108 A1 | 8/2008 | Kimura |
| 2008/0215048 A1* | 9/2008 | Hafner ............... A61B 17/2841 606/42 |
| 2008/0300613 A1 | 12/2008 | Shelton, IV et al. |
| 2009/0012520 A1 | 1/2009 | Hixson et al. |
| 2009/0118751 A1 | 5/2009 | Wiener et al. |
| 2009/0182327 A1 | 7/2009 | Unger |
| 2009/0240246 A1 | 9/2009 | Deville et al. |
| 2010/0130977 A1 | 5/2010 | Garrison et al. |
| 2010/0249769 A1 | 9/2010 | Nau, Jr. et al. |
| 2010/0249776 A1 | 9/2010 | Kerr |
| 2010/0274244 A1 | 10/2010 | Heard |
| 2011/0009890 A1 | 1/2011 | Palmer et al. |
| 2011/0015660 A1 | 1/2011 | Wiener et al. |
| 2011/0054472 A1 | 3/2011 | Romero |

(56) References Cited

U.S. PATENT DOCUMENTS

| | | |
|---|---|---|
| 2011/0060356 A1 | 3/2011 | Reschke et al. |
| 2011/0087218 A1 | 4/2011 | Boudreaux et al. |
| 2011/0218530 A1 | 9/2011 | Reschke |
| 2011/0238067 A1 | 9/2011 | Moses et al. |
| 2011/0257680 A1 | 10/2011 | Reschke et al. |
| 2012/0022526 A1 | 1/2012 | Aldridge et al. |
| 2012/0172873 A1 | 7/2012 | Artale et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009317 U1 | 8/2007 |
| DE | 19738457 B4 | 1/2009 |
| DE | 102004026179 B4 | 1/2009 |
| EP | 1159926 A3 | 3/2003 |
| EP | 1532932 A1 | 5/2005 |
| EP | 1609430 | 12/2005 |
| EP | 1810625 A1 | 7/2007 |
| JP | 61-501068 | 9/1984 |
| JP | 10-24051 A | 1/1989 |
| JP | 6-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | 8-56955 | 3/1996 |
| JP | 08252263 A | 10/1996 |
| JP | 9-10223 | 1/1997 |
| JP | H10508781 A | 9/1998 |
| JP | 11-070124 A | 3/1999 |
| JP | 11-169381 A | 6/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2006102514 A | 4/2006 |
| SU | 401367 A1 | 10/1973 |
| WO | 0036986 A1 | 6/2000 |
| WO | 0154604 A1 | 8/2001 |
| WO | 2005/110264 A2 | 11/2005 |

OTHER PUBLICATIONS

U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument" Innovations That Work, .quadrature.Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, No. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicoletomy Using the LigaSure Vessel Sealing System" Innovations That Work,. quadrature.Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Intl Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
U.S. Appl. No. 09/387,883, filed Sep. 1, 1999.
U.S. Appl. No. 09/591,328, filed Jun. 9, 2000.
U.S. Appl. No. 12/336,970, filed Dec. 17, 2008.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.

(56) References Cited

OTHER PUBLICATIONS

U.S. Appl. No. 12/775,553, filed May 7, 2010.
U.S. Appl. No. 12/786,589, filed May 25, 2010.
U.S. Appl. No. 12/791,112, filed Jun. 1, 2010.
Japanese Office Action and English Language translation issued in Appl. No. JP 2015-121663 dated Apr. 15, 2016.
Extended European Search Report from Appl. No. 16154503.3 dated May 24, 2016.
ITT Cannon Switch Products, Switches 1997: K12 Key Switch, ITT Cannon Product Catalog, 1997.
Australian Examination Report issued in Appl. No. AU 2016201119 dated Aug. 25, 2017.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Intl Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No. 11007972.0 dated Dec. 20, 2011.
Australian Examination Report from Application No. AU2014203675 dated Jun. 15, 2015.
Extended European Search Report for EP 13 75 7413 dated Sep. 14, 2015.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Intl Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Intl Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Intl Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 0152267.2 dated Jun. 15, 2009.
Notice of Final Rejection issued in Japanese Appl. No. JP 2015-121663 dated Nov. 9, 2016.
Japanese Office Action issued in Appl. No. JP 2015-121663 dated Jan. 31, 2018, together with English language translation (8 pages).

* cited by examiner

BLADE DEPLOYMENT MECHANISMS FOR SURGICAL FORCEPS

CROSS-REFERENCE TO RELATED APPLICATIONS

The present application is a continuation of U.S. patent application Ser. No. 14/692,920 filed Apr. 22, 2015, which is a continuation of U.S. patent application Ser. No. 12/896,100 filed Oct. 1, 2010, now U.S. Pat. No. 9,017,372, the entire contents of each of which are incorporated herein by reference.

BACKGROUND

The present disclosure relates to surgical forceps and, more particularly, to blade deployment mechanisms for use in surgical forceps for sealing and dividing tissue.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

In accordance with one embodiment of the present disclosure, a forceps is provided. The forceps includes first and second shaft members. Each of the shaft members has a jaw member disposed at a distal end thereof. One (or both) of the jaw members is moveable relative to the other from an open position to a closed position for grasping tissue therebetween. One (or both) of the jaw members is configured for reciprocation of a blade therethrough. A trigger assembly is configured for selectively translating the blade between a retracted position and an extended position. In the extended position, the blade extends partially, or entirely, through the jaw member(s). The trigger assembly includes a rotatable trigger, one or more linkages and an interference member. The linkage(s) is coupled at a first end to the rotatable trigger and at a second end to the blade such that rotation of the trigger effects translation of the blade between the retracted position and the extended position. The interference member is moveable between a locked position and an unlocked position. When the jaw members are in the open position, the interference member is in the locked position engaging the linkage(s) to inhibit translation of the blade from the retracted position to the extended position. When the jaw members are moved to the closed position, the interference member is moved to the unlocked position, permitting translation of the blade.

In one embodiment, a biasing member is provided for biasing the blade toward the retracted position. The interference member may also be biased toward the locked position.

In another embodiment, the interference member is rotatable about a pivot between the locked position and the unlocked position. In the locked position, as mentioned above, the interference member engages the linkage(s) to inhibit translation of the blade while, in the unlocked position, the interference member is disengaged from the linkage(s) and, thus, translation of the blade is permitted.

In yet another embodiment, a tab extending from the second shaft member contacts the interference member to rotate the interference member from the locked position to the unlocked position, thereby disengaging the interference member from the linkage(s) upon movement of the jaw members to the closed position. Alternatively, the second shaft member may contact a tab extending from the interference member upon movement of the jaw members to the closed position to rotate the interference member from the locked position to the unlocked position, thereby disengaging the interference member from the linkage(s).

In still another embodiment, one (or both) of the jaw members is adapted to connect to a source of electrosurgical energy. Accordingly, an actuator may be provided for controlling the supply of electrosurgical energy to the jaw members. In particular, the first shaft member may include an actuator and the second shaft member may be configured such that, upon application of a pre-determined closure force to the jaw members, the second shaft member activates the actuator to supply electrosurgical energy to the jaw members.

In accordance with another embodiment of the present disclosure, a forceps is provided. As in the previous embodiment, the forceps includes first and second shaft members, each having a jaw member disposed at a distal end thereof. One (or both) of the jaw members is moveable from an open position to a closed position for grasping tissue therebetween. One (or both) of the jaw members is configured for reciprocation of a blade therethrough. A trigger assembly is configured for selectively translating the blade between a retracted position and an extended position. The trigger assembly includes a trigger, an arm, a cantilever, and one or more linkages. The arm has a first end that is coupled to the trigger and a free second end. The cantilever defines an engagement recess therein and is rotatable about a pivot between a first position and a second position. The linkage(s) is coupled at a first end to the cantilever and at a second end to the blade. A tab extends from the second shaft member. The tab is configured to urge the free end of the arm into the engagement recess of the cantilever upon movement the jaw members to the closed position such that proximal translation of the trigger rotates the cantilever from the first position to the second position to translate the blade distally from the retracted position to the extended position.

In one embodiment, a biasing member is provided for biasing the blade toward the retracted position. A biasing member may also be provided for biasing the trigger toward an initial position. Further, the arm may be a flat spring and, optionally, may be biased away from the engagement recess of the cantilever.

In another embodiment, the first shaft includes a cantilever groove defined therein. The cantilever groove is configured to permit rotation of the cantilever between the first position and the second position.

In yet another embodiment, one (or both) of the jaw members is adapted to connect to a source of electrosurgical energy.

In still another embodiment, the engagement recess of the cantilever is configured such that, when the cantilever is rotated to the second position, the free end of the arm is disengaged from the engagement recess.

In accordance with yet another embodiment of the present disclosure, a forceps is provided. The forceps includes first and second shaft members each having a jaw member. One (or both) of the jaw members is moveable from an open position to a closed position for grasping tissue therebetween. One (or both) of the jaw members is configured for reciprocation of a blade therethrough. A trigger assembly configured for selectively translating the blade between a retracted position and an extended position includes a rotatable trigger, one or more linkages and a piston. The linkage(s) is coupled at a first end to the rotatable trigger and at a second end to the blade such that rotation of the trigger effects translation of the blade between the retracted position and the extended position. The piston is coupled at a first end to the linkage(s) and at a second end to the second shaft member. The piston is moveable between a contracted position and an extended position. When in the extended position, the piston inhibits translation of the blade from the retracted position to the extended position.

A first biasing member may be provided for biasing the blade toward the retracted position and/or a second biasing member may be disposed within the piston for biasing the piston toward the contracted position. The second biasing member may be a compression spring.

In another embodiment, the piston is pivotably coupled to the one or more linkages.

In yet another embodiment, the piston is moved to the extended position upon movement of the jaw members to the open position such that the blade is inhibited from translating to the extended position when the jaw members are in the open position. The open position of the jaw members may correspond to a position wherein the jaw members are angled about at least 5 degrees with respect to one another.

In still another embodiment, the piston is further configured to return the blade to the retracted position when the jaw members are moved from the closed position to the open position.

BRIEF DESCRIPTION OF THE DRAWINGS

Various embodiments of the subject forceps are described herein with reference to the drawings wherein.

DETAILED DESCRIPTION

Figure 1:
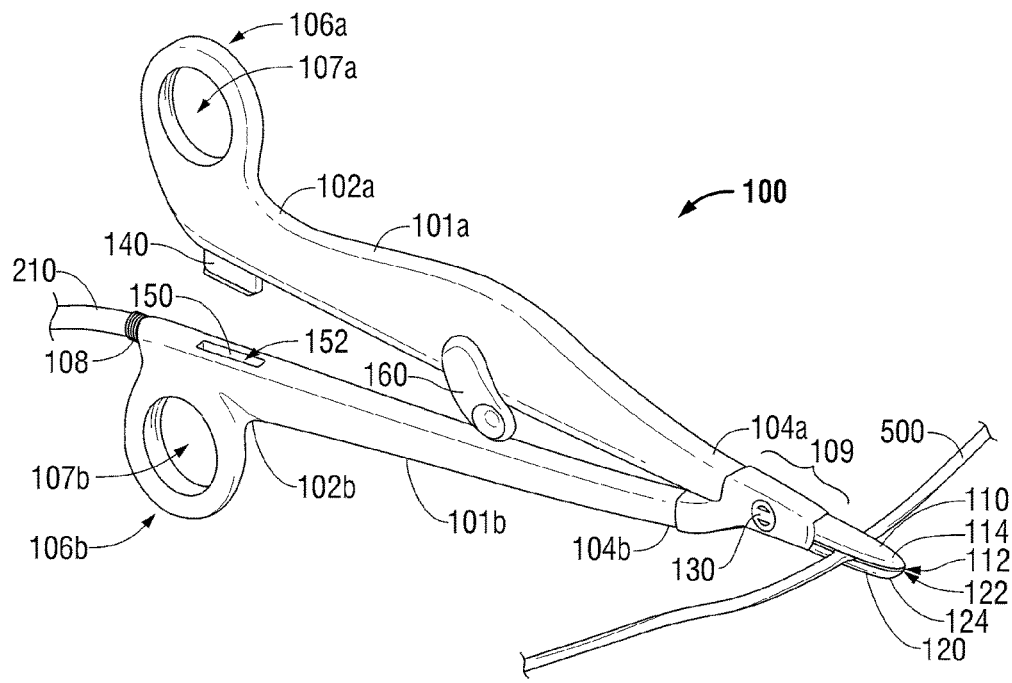
FIG. 1 is a side, perspective view of a forceps according to an embodiment of the present disclosure.

Referring initially to FIG. 1, a forceps 100 includes two elongated shaft members 101a, 101b each having a proximal end 102a, 102b and a distal end 104a, 104b, respectively. In the drawings and in the descriptions which follow, the term "proximal," as is traditional, will refer to the end of the forceps 100 that is closer to the user, while the term "distal" will refer to the end that is further from the user.

The forceps 100 includes an end effector assembly 109 attached to distal ends 104a, 104b of shaft members 101a, 101b, respectively. As explained in more detail below, the end effector assembly 109 includes a pair of opposing jaw members 110, 120 that are pivotably connected about a pivot pin 130.

Each shaft member 101a, 101b includes a handle 106a, 106b disposed at the proximal end 102a, 102b, respectively, thereof. Each handle 106a, 106b defines a finger hole 107a, 107b, respectively, therethrough for receiving a finger of the user. As can be appreciated, finger holes 107a, 107b facilitate movement of the shaft members 101a, 101b relative to one another which, in turn, pivots the jaw members 110, 120 from an open position, wherein the jaw members 110, 120 are disposed in spaced-apart relation relative to one another to a closed position (FIG. 1), wherein the jaw members 110, 120 cooperate to grasp tissue 500 therebetween.

With continued reference to FIG. 1, one of the shafts, e.g., shaft member 101b, includes a proximal shaft connector 108 that is designed to connect the forceps 100 to a source of electrosurgical energy such as an electrosurgical generator (not shown) or other suitable power source. Proximal shaft connector 108 secures an electrosurgical cable 210 to the forceps 100 such that the user may selectively apply electrosurgical energy from the generator (not shown) to either (or both) of jaw members 110, 120 as needed.

As mentioned above, the two opposing jaw members 110 and 120 of the end effector assembly 109 are pivotable about pivot pin 130 from the open position to the closed position for grasping tissue 500 therebetween. Jaw member 110 includes an insulated outer housing 114 that is configured to mechanically engage an electrically conductive sealing surface 112 of jaw member 110. Similarly, jaw member 120 includes an insulated outer housing 124 that is configured to mechanically engage an electrically conductive sealing surface 122 of jaw member 120. Electrically conductive sealing surfaces 112 and 122 are opposed to one another, such that, upon activation, electrosurgical energy may be supplied to the electrically conductive sealing surfaces 112 and 122 for sealing tissue 500 disposed between the jaw members 110 and 120. More particularly, a first electrical potential may be provided to first jaw member 110 and a second electrical potential may be provided to second jaw member 120 to conduct energy between the sealing surfaces 112, 122 of jaw members 110, 120, respectively, to seal tissue 500 disposed therebetween.

A tab 140 disposed at proximal end 102a of shaft member 101a extends from shaft member 101a toward shaft member 101b. A corresponding recess 150 is defined within shaft member 101b toward proximal end 102b thereof and is configured to receive tab 140 therein. Upon approximation of shaft members 101a, 101b, e.g., when jaw members 110, 120 are moved to the closed position, tab 140 enters recess 150. Upon further approximation of shaft members 101a, 101b, e.g., upon application of a pre-determined closure force to jaw members 110, 120, tab 140 is advanced further into recess 150 to depress actuator 152 disposed therein. Actuator 152 controls the supply of electrosurgical energy to jaw members 110, 120 such that, upon depression of actuator 152, electrosurgical energy is supplied to sealing surface 112 and/or sealing surface 122 of jaw members 110, 120, respectively, to seal tissue 500 grasped therebetween. Other more standardized activation switches are also contemplated, e.g., finger switch, toggle switch, foot switch, etc.

Figure 2:
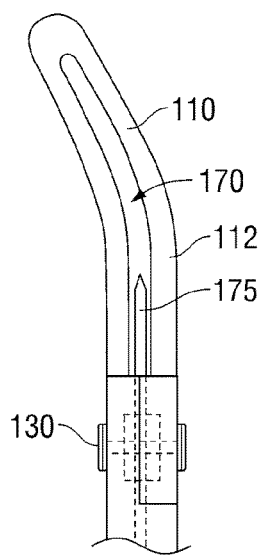
FIG. 2 is a top view of a jaw member of the forceps of FIG. 1.

As best seen in FIG. 2, jaw member 110 includes a blade slot, or blade channel 170 extending therethrough. The blade channel 170 is configured for reciprocation of a cutting mechanism, e.g., a blade 175, therethrough. As shown, blade channel 170 is defined completely within jaw member 110. However, the blade channel 170 may be formed when two opposing blade channels defined within jaw members 110, 120 come together upon pivoting of jaw members 110, 120 to the closed position. Further, the blade channel 170 may be configured to facilitate and/or enhance cutting of tissue during reciprocation of the cutting blade 175 in the distal direction.

Referring again to FIG. 1, in conjunction with FIG. 2, shaft member 101a of forceps 100 includes a rotatable trigger 160 coupled thereto, although trigger 160 may be disposed on shaft member 101b. Trigger 160 is rotatable about a pivot for advancing blade 175 from shaft member 101a into blade channel 170, to divide tissue 500 grasped between jaw members 110, 120. In other words, axial rotation of trigger 160 effects longitudinal translation of blade 175. More specifically, trigger 160 is rotatable between a first, or retracted position, wherein blade 175 is disposed within shaft member 101a, and a second, or extended position, wherein blade 175 extends at least partially through blade channel 170. As will be described in greater detail below, trigger 160 and trigger assembly 180 may be configured to inhibit advancement of blade 175 through blade channel 170 when jaw members 110, 120 are in the open position and/or may be biased toward the first position such that the blade 175 is returned to the retracted position within shaft member 101a once blade 175 has been advanced through blade channel 170.

Figure 3A:
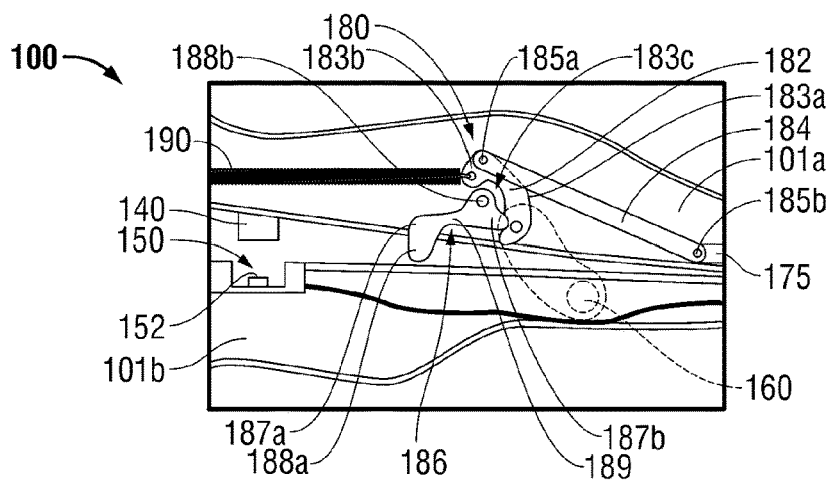
FIG. 3A is a side view of the forceps of FIG. 1 shown in a first position, where a portion of the handle has been removed to show the internal components therein.
Figure 3B:
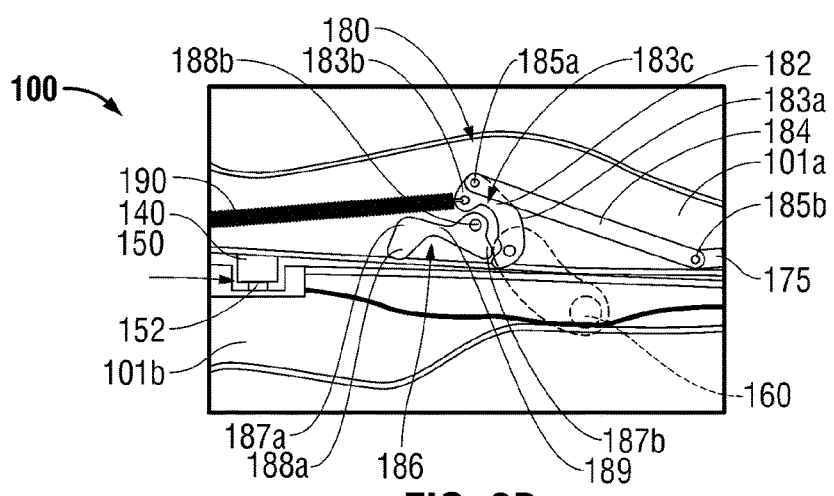
FIG. 3B is a side view of the forceps of FIG. 3A shown transitioning between the first position and a second position, where a portion of the handle has been removed to show the internal components therein.
Figure 3C:
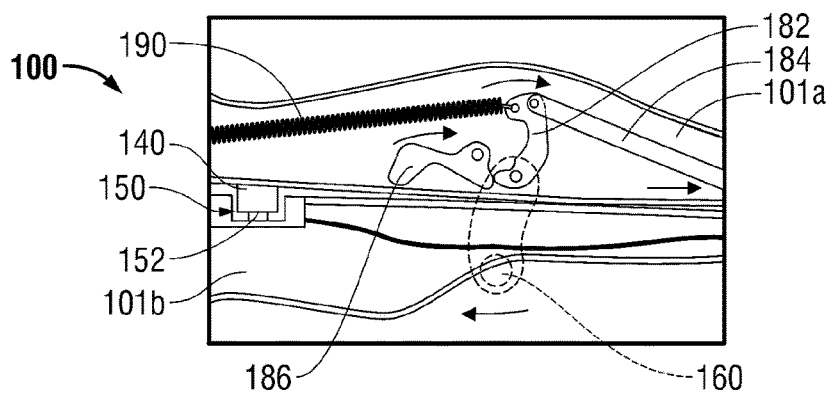
FIG. 3C is a side view of the forceps of FIG. 3A shown in a second position, where a portion of the handle has been removed to show the internal components therein.

With reference now to FIG. 3A-3C, trigger assembly 180 of forceps 100 includes trigger 160, pivoting linkage 182, bar linkage 184, interference member 186 and biasing spring 190. Trigger 160 is pivotably coupled to a first end 183a of pivoting linkage 182. Pivoting linkage 182 is pivotably coupled at second end 183b thereof to first end 185a of bar linkage 184. Biasing spring 190 is engaged to second end 183b of pivoting linkage 182 such that, as will be described in detail below, pivoting linkage 182 and, thus, trigger 160, are biased in the first, or retracted position, as shown in FIG. 3A. Bar linkage 184 extends distally from trigger assembly 180, ultimately engaging blade 175 at second end 185b of bar linkage 184. Interference member 186 is pivotable about a pivot 189 and includes a proximal end 187a and a distal end 187b, each of which includes a protrusion 188a, 188b, respectively, extending therefrom.

As shown in FIG. 3A, trigger assembly 180 is disposed in a first, at-rest position corresponding to the open, or spaced-apart position of jaw members 110, 120 (FIG. 1). In the first position of trigger assembly 180, trigger 160 and pivoting linkage 182 are disposed in the retracted position such that bar linkage 184 is disposed in a proximal-most position wherein blade 175 is disposed completely within shaft member 101a of forceps 100, or at least proximal to tissue engaging surfaces 112, 122 of jaw members 110, 120, respectively. Further, when jaw members 110, 120 (FIG. 1) are in the open position, protrusion 188b at distal end 187b of interference member 186, as shown in FIG. 3A, is disposed within recess 183c of pivoting linkage 182, inhibiting pivoting linkage 182 from pivoting and, as a result, inhibiting rotation of trigger 160 to the extended position for advancing blade 175 through blade channel 170 (FIG. 2). Put more generally, interference member 186 functions as a locking mechanism, inhibiting blade 175 from being deployed when jaw members 110, 120 (FIG. 1) are in the open position. Interference member 186 may be biased toward this "locked" position. As will be described below, interference member 186 is configured to permit deployment of blade 175 into blade channel 170 (FIG. 2) to cut tissue disposed between jaw members 110, 120 (FIG. 1) when jaw members 110, 120 (FIG. 1) are moved to the closed position.

Referring now to FIG. 3B, which shows forceps 100 wherein shaft members 101a, 101b have been approximated with respect to one another to move jaw members 110, 120 (FIG. 1) to the closed position. As discussed above, upon movement of jaw members 110, 120 (FIG. 1) to the closed position, tab 140, which extends from shaft member 101a, is advanced into recess 150 of shaft member 101b. Upon further approximation of jaw members 110, 120, e.g., upon application of a pre-determined closure force (or range of closure forces) to jaw members 110, 120, tab 140 is urged further into recess 150 to depress actuator 152 and supply (or allow the user to selectively supply via a trigger or other switch) electrosurgical energy to sealing surfaces 112, 122 of jaw members 110, 120 (FIG. 1) for sealing tissue 500

(FIG. 1) grasped therebetween. Actuator 152 may be configured to supply electrosurgical energy to sealing surfaces 112, 122 of jaw members 110, 120 (FIG. 1) for a pre-determined length of time (either a fixed or adjustable length of time) to adequately form a tissue seal. Alternatively, actuator 152, when depressed, may be configured to supply electrosurgical energy to sealing surfaces 112, 122 (FIG. 1) continuously, so long as the pre-determined closure force (or range of closure forces) applied to jaw members 110, 120 (FIG. 1) is maintained. Again, actuator 152 may simply act as an electrical toggle switch that only allows the delivery of energy when jaw members 110, 120 (FIG. 1) are closed.

As shown in FIG. 3B, upon approximation of shaft members 101a, 101b, the outer surface of shaft member 101b contacts protrusion 188a at proximal end 187a of interference member 186, rotating interference member 186 about pivot 189 in a clockwise direction. As interference member 186 is rotated, protrusion 188b at distal end 187b of interference member 186 is disengaged from recess 183c of pivoting linkage 182. Thus, as protrusion 188b of interference member 186 is moved out of recess 183c defined within pivoting linkage 182, pivoting linkage 182 and trigger 160, are "unlocked," or permitted to rotate. Accordingly, with jaw members 110, 120 (FIG. 1) in the unlocked position, trigger 160 may be rotated to advance blade 175 distally between jaw members 110, 120 (FIG. 1) to cut tissue 500 (FIG. 1) disposed therebetween. However, at this point, due to biasing spring 190, trigger 160 and blade 175 remain in the retracted position.

Turning now to FIG. 3C, once electrosurgical energy has been conducted through tissue 500 (FIG. 1) grasped between sealing surfaces 112, 122 of jaw members 110, 120 (FIG. 1) to seal tissue 500 (FIG. 1) (or where it is desired to simply grasp and divide tissue), blade 175 may be advanced through blade channel 170 (FIG. 2) to cut tissue 500 (FIG. 1) grasped between jaw members 110, 120 (FIG. 1). More particularly, in order to advance blade 175 into channel 170, trigger 160 is rotated in a clockwise direction. Rotation of trigger 160 effects similar clockwise rotation of pivoting linkage 182, against the bias of biasing spring 190. As pivoting linkage 182 is rotated, second, or proximal end 183b of pivoting linkage 182 is moved distally and, since bar linkage 184 is coupled to second end 183b of pivoting linkage 182, bar linkage 184 is also translated distally. The distal translation of bar linkage 184, in turn, effects distal translation of blade 175 from shaft member 101a into blade channel 170 (FIG. 2). In other words, rotation of trigger 160 rotates pivoting linkage 182 which, in turn, advances bar linkage 184 distally such that blade 175 is advanced into blade channel 170 (FIG. 2) defined within jaw member 110 to cut tissue 500 grasped between jaw members 110, 120 (FIG. 1).

Upon release of trigger 160, pivoting linkage 182 is rotated counter-clockwise under the bias of biasing spring 190 such that bar linkage 184 and blade 175 are returned proximally to the retracted position within shaft member 101a. In other words, trigger assembly 180 is configured such that blade 175 is automatically retracted after deployment through blade channel 170 (FIG. 2). At this point, with tissue 500 having been sealed and divided, and with blade 175 in the retracted position, jaw members 110, 120 may be moved to the open, or spaced-apart position to release tissue 500 (FIG. 1) such that forceps 100 may be withdrawn from the surgical site. As shaft members 101a, 101b are moved apart from one another, interference member 186 is returned to the "locked" position. More specifically, as shaft member 101b is moved apart from protrusion 188a of interference member 186, interference member 186 is rotated in a counter-clockwise direction such that protrusion 188b is moved back into engagement within recess 183c of pivoting linkage 182 to once again "lock," or inhibit deployment of blade 175.

Figure 4A:
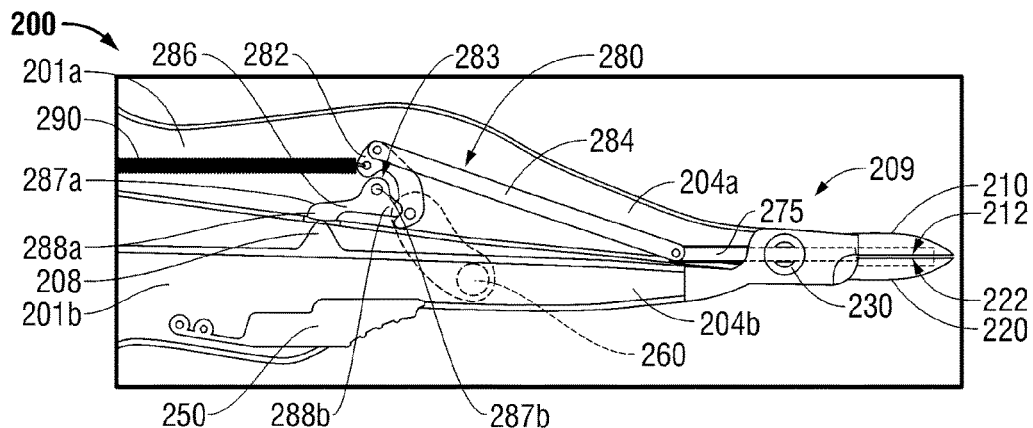
FIG. 4A is a side view of another embodiment of a forceps in accordance with the present disclosure shown in a first position, where a portion of a handle has been removed to show the internal components therein.
Figure 4B:
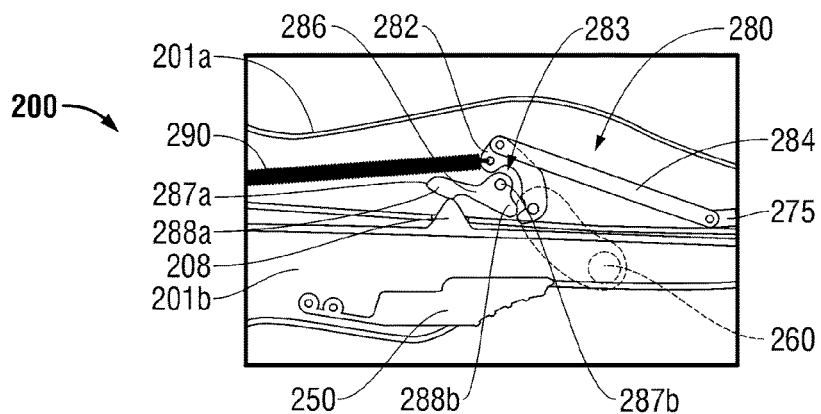
FIG. 4B is a side view of the forceps of FIG. 1 transitioning between the first position and a second position, where a portion of the handle has been removed to show the internal components therein.
Figure 4C:
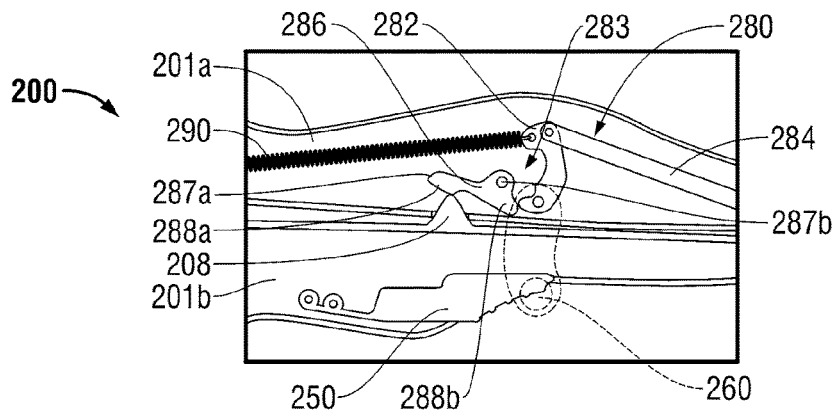
FIG. 4C is a side view of the forceps of FIG. 1 in the second position, where a portion of the handle has been removed to show the internal components therein.

Turning now to FIGS. 4A-4C, another embodiment of a forceps, forceps 200, is shown. Forceps 200 is similar to forceps 100, discussed above, and includes two elongated shaft members 201a, 201b having an end effector assembly 209 attached to distal ends 204a, 204b, respectively, thereof. The end effector assembly 209 includes a pair of pivotably connected opposing jaw members 210, 220 and is configured such that movement of the shaft members 201a, 201b relative to one another pivots jaw members 210, 220 between an open position and a closed position for grasping tissue therebetween.

Continuing with reference to FIGS. 4A-4C, jaw members 210, 220 each include an electrically conductive sealing surface 212, 222, respectively, disposed thereon. Electrically conductive sealing surfaces 212, 222 are opposed to one another, such that, upon activation, electrosurgical energy may be supplied to the electrically conductive sealing surfaces 212, 222 for sealing tissue grasped between jaw members 210, 220. An actuator 250 disposed on shaft member 201b is provided for controlling the supply of electrosurgical energy to sealing surfaces 212, 222 of jaw members 210, 220, respectively. In other words, actuator 250 is selectively depressible to supply electrosurgical energy to sealing surfaces 212, 222.

Forceps 200 further includes a trigger 260 coupled to a trigger assembly 280 disposed within one of shaft members 201a, 201b, e.g., shaft member 201a. Trigger 260 is configured for selectively advancing a blade 275 between jaw members 210, 220 to divide tissue grasped therebetween. Accordingly, as in the previous embodiment, forceps 200 may include a blade channel (not shown) defined within one (or both) of jaw members 210, 220 and configured to permit translation of blade 275 therethrough for dividing tissue grasped between jaw members 210, 220.

Trigger assembly 280 of forceps 200 is similar to trigger assembly 180 of forceps 100 and includes a pivoting linkage 282, a bar linkage 284, an interference member 286 and a biasing spring 290. Interference member 286 includes a proximal end 287a and a distal end 287b. Proximal end 287a of interference member 286 includes a recessed portion 288a configured to receive protrusion 208 of shaft member 201b therein, while distal end 287b of interference member 286 includes a protrusion 288b extending therefrom. As in the previous embodiment, trigger 260 is coupled to pivoting linkage 282 which, in turn, is coupled to bar linkage 284. Biasing spring 290 biases pivoting linkage 282 and trigger 260 in a first, or retracted position, as shown in FIG. 4A. Bar linkage 284 extends distally from trigger assembly 280 to engage blade 275 such that, upon rotation of trigger 260 in a clockwise direction, pivoting linkage 282 is likewise rotated in a clockwise direction, advancing bar linkage 284 distally which, in turn, translates blade 275 distally from shaft member 201a through jaw members 210, 220 to cut tissue disposed therebetween.

With reference now to FIG. 4A, trigger assembly 280 is shown in a "locked" position wherein protrusion 288b of interference member 286 is engaged within recess 283 of pivoting linkage 282, inhibiting pivoting linkage 282 and, thus, trigger 260 from being rotated to deploy blade 275. This "locked" position of trigger assembly 280 corresponds to the open, or spaced-apart position of jaw members 210, 220.

As shown in FIG. 4B, upon approximation of shaft members 201a, 201b, i.e., upon movement of jaw members 210, 220 to the closed position to grasp tissue therebetween, protrusion 208, which extends from shaft member 201b, is moved into engagement with recessed portion 288a of interference member 286, urging interference member 286 to rotate in a clockwise direction such that protrusion 288b of interference member 286 is disengaged from recess 283 of pivoting linkage 282, thereby "unlocking" trigger assembly 280. Accordingly, once jaw members 210, 220 are moved to the approximated position, trigger assembly 280 is "unlocked" and, thus, trigger 260 may be rotated to advance blade 275 between jaw members 210, 220, to cut tissue grasped therebetween. However, prior to deployment, e.g., prior to rotation of trigger 260, blade 275 remains in the retracted position due to the bias of biasing spring 290.

When it is desired to advance blade 275 to cut tissue grasped between jaw members 210, 220, trigger 260 is rotated in a clockwise direction, rotating pivoting linkage 282 in a clockwise direction which, in turn, advances bar linkage 284 and blade 275 distally such that blade 275 is translated between jaw members 210, 220 to cut tissue grasped therebetween.

Upon release of trigger 260, pivoting linkage 282 is rotated in a counter-clockwise direction under the bias of biasing spring 290 such that blade 275 is translated proximally to the retracted position within shaft member 201a. At this point, jaw members 210, 220 may be moved to the open, or spaced-apart position and forceps 200 may be withdrawn from the surgical site. As shaft members 201a, 201b are moved apart from one another, protrusion 208 in shaft member 201b is disengaged from recessed portion 288a of interference member 386, allowing protrusion 288b of interference member 286 to engage pivoting linkage 282, locking trigger assembly 280 and preventing deployment of blade 275.

Figure 5A:
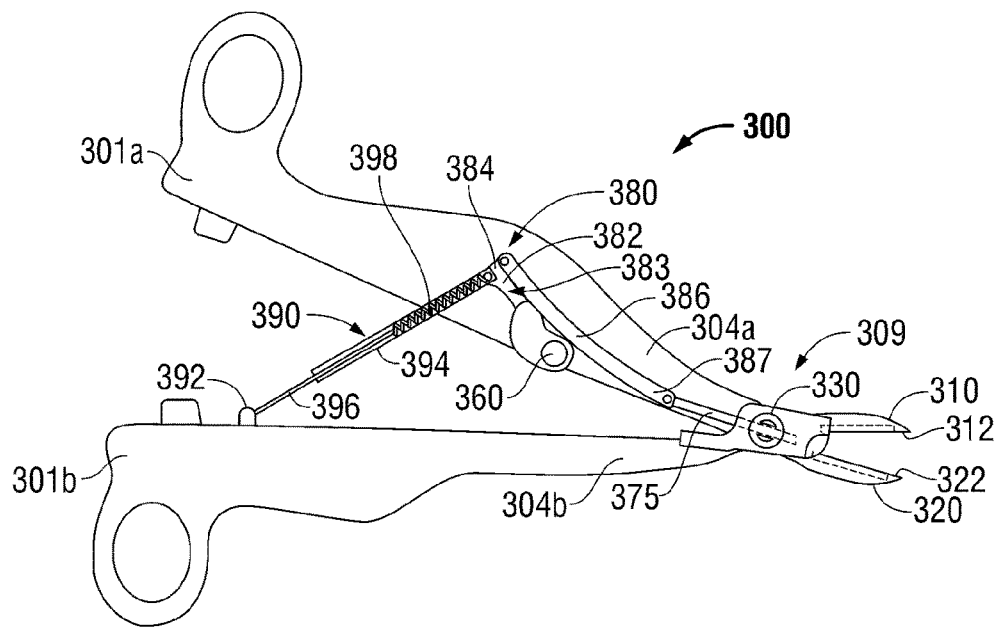
FIG. 5A is a side view of another embodiment of a forceps in accordance with the present disclosure shown in a first position, where a portion of a handle has been removed to show the internal components therein.
Figure 5B:
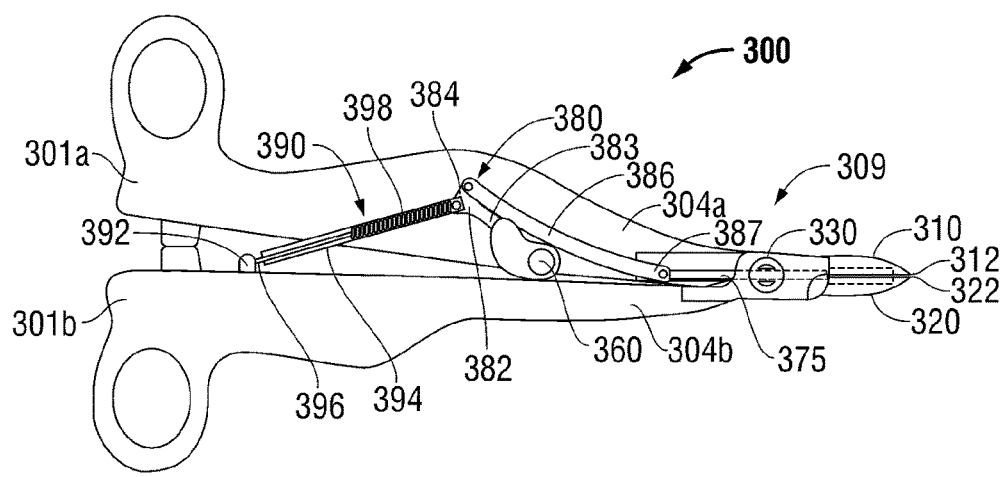
FIG. 5B is a side view of the forceps of FIG. 5A shown in a second position, where a portion of the handle has been removed to show the internal components therein.
Figure 5C:
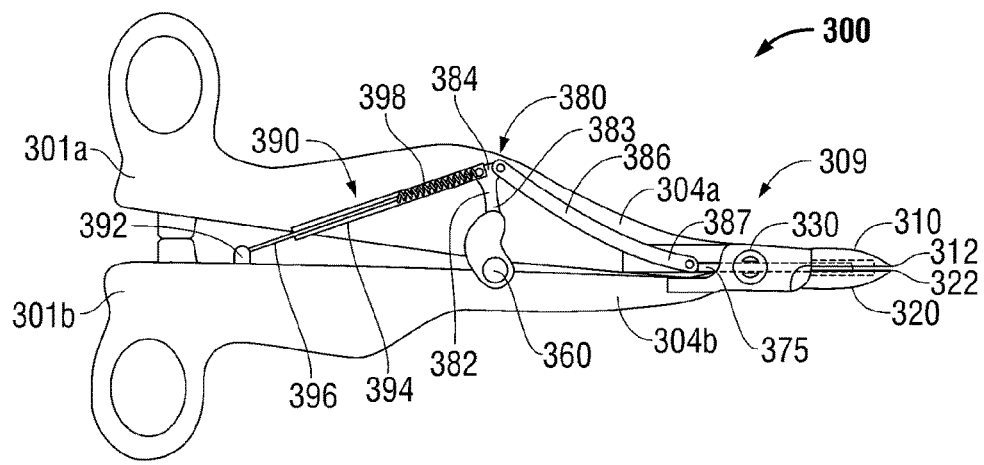
FIG. 5C is a side view of the forceps of FIG. 5A shown in a third position, where a portion of the handle has been removed to show the internal components therein.

Another embodiment of a forceps in accordance with the present disclosure, forceps 300, is shown in FIGS. 5A-5C. Forceps 300 is similar to the previous embodiments and generally includes a pair of shaft members 301a, 301b having an end effector assembly 309 disposed at distal ends 304a, 304b, respectively, thereof. The end effector assembly 309 includes a pair of jaw members 310, 320 that are pivotable about pivot 330 between an open position and a closed position upon movement of the shaft members 301a, 301b relative to one another between a spaced-apart position and an approximated position. Jaw members 310, 320 may include opposed electrically conductive sealing surfaces 312, 322, respectively, disposed thereon. One or both of electrically conductive sealing surfaces 312, 322 may be adapted to connect to a source of electrosurgical energy (not shown) for sealing tissue grasped between jaw members 310, 320.

Forceps 300 further includes a trigger 360 disposed on shaft member 301a (although trigger 360 may be disposed on shaft member 301b) and a trigger assembly 380 disposed therein. As in the previous embodiments, trigger assembly 380 is configured for selectively translating a blade 375 between a retracted position, wherein blade 375 is disposed within shaft member 301a, and an extended position, wherein blade 375 extends between jaw members 310, 320 to cut tissue grasped therebetween.

Trigger assembly 380 includes a three-way linkage 382, a bar linkage 386, and a piston assembly 390. Three-way linkage 382 is coupled at a first end 383 thereof to trigger 360 and at a second end 384 thereof to both bar linkage 386 and piston assembly 390. Bar linkage 386 extends distally from three-way linkage 382 and is engaged to blade 375 at distal end 387 of bar linkage 386. Piston assembly 390 extends proximally from three-way linkage 382 and is pivotably engaged to piston base 392 disposed on shaft member 301b. Piston assembly 390 further includes an outer shaft 394 and an inner shaft 396 that is slidably receivable within outer shaft 394 between an extended position, wherein inner shaft 396 extends from outer shaft 394, and a contracted position, wherein inner shaft 396 is substantially disposed within outer shaft 394. A biasing member, e.g., a compression spring 398, configured to bias piston assembly 390 toward the contracted position may also be provided.

With reference to FIGS. 5B-5C, in order to deploy blade 375, jaw members 310, 320 are first moved to the closed position. Next, trigger 360 is rotated in a clockwise direction which, in turn, rotates pivoting linkage 382 in a clockwise direction. As pivoting linkage 382 is rotated in a clockwise direction, second end 384 of pivoting linkage 382 is moved distally, translating bar linkage 386 distally, as best shown in FIG. 5C. At the same time, piston assembly 390 is extended, i.e., inner shaft 396 and outer shaft 396 are moved from the contracted position to the extended position against the bias of compression spring 398 (FIG. 5A). The extension of piston assembly 390 allows pivoting linkage 382 to rotate in a clockwise direction and, thus, allows second end 384 of pivoting linkage 382 to move distally. This distal movement of second end 384 of pivoting linkage 382 translates bar linkage 386 distally, which, in turn, translates blade 375 distally from shaft member 301a through jaw members 310, 320 to cut tissue grasped therebetween.

As shown in FIG. 5C, and as mentioned above, piston assembly 390 is moved to the extended position to permit blade 375 to be advanced to the extended position. Accordingly, when trigger 360 is released, blade 375 is returned to the retracted position as piston assembly 390 is returned to the contracted position under the bias of compression spring 398 (FIG. 5A) disposed within outer shaft 394 of piston assembly 390. More particularly, when trigger 360 is released, compression spring 398 (FIG. 5A) biases position assembly 390 back to the contracted position, thereby moving second end 384 of pivoting linkage 382 proximally which, in turn, translates bar linkage 386 and blade 375 proximally back to the retracted position. At the same time, the proximal movement of second end 384 of pivoting linkage 382 causes pivoting linkage 382 to rotate in a counter-clockwise direction which, in turn, causes trigger 360 to rotate in a counter-clockwise direction, to the initial position (FIG. 5B). Put more generally, when trigger 360 is released, blade 375 and trigger assembly 380 are returned to the retracted position. Once blade 375 is returned to the retracted position, jaw members 310, 320 may be moved to the spaced-apart position and forceps 300 may be removed from the surgical site.

However, if trigger 360 and/or blade 375 are retained, or become stuck in the extended position, piston assembly 390 returns blade 375 to the retracted position upon movement of jaw members 310, 320 from the approximated position to the spaced-apart, thereby helping to ensure that blade 375 is not exposed when jaw members 110, 120 are disposed in the spaced-apart position. More particularly, as mentioned above, when blade 375 is in the extended position, piston assembly 390 is in the extended position. When in the extended position, piston assembly 390 is inhibited from extending further. However, moving shaft members 301a, 301b apart from one another while blade 375 is in the extended position would require further extension of piston assembly 390 (since moving shaft members 301a, 301b apart from one another moves piston base 392, which is attached to one end of piston assembly 390, and second end 384 of pivoting linkage 382, which is attached to the other end of piston assembly 390, apart from one another). Therefore, in order to accommodate the movement of shaft members 301a, 301b apart from one another, e.g., from the approximated position to the spaced-apart position, piston assembly 390 pulls second end 384 of pivoting linkage 382 proximally, thereby translating blade 375 proximally from the extended position back to the retracted position as jaw members 310, 320 are moved apart from one another. As such, upon movement of jaw members 310, 320 from the approximated position to the spaced-apart position, piston assembly 390 returns blade 375 to the retracted position within shaft 301a. Alternatively, piston assembly 390 may be configured to inhibit jaw members 310, 320 from being moved from the approximated position to the spaced-apart position when blade 375 is disposed in the extended position.

With reference to FIG. 5A, forceps 300 is shown wherein shaft members 301a, 301b and, thus, jaw members 310, 320 are disposed in the open, or spaced-apart position. When jaw members 310, 320 are in the open position, piston assembly 390, which extends from shaft member 301a to shaft member 301b, is disposed in the extended position. In the extended position, as mentioned above, piston assembly 390 is inhibited from extending further. As a result, piston assembly 390, when in the extended position, inhibits pivoting linkage 382 from rotating, i.e., piston assembly 390 inhibits second end 384 of pivoting linkage 382 from moving distally, as is required upon rotation of pivoting linkage 382. Accordingly, since pivoting second end 384 is inhibited from moving distally, linkage 382 is thereby inhibited from rotating and, in turn, trigger 360 is inhibited from rotating. Thus, when piston assembly 390 is in the extended position, blade 375 is inhibited from being deployed, or extended into the open jaw members 310, 320.

The open position of jaw members 310, 320 may be defined as the position wherein jaw members 310, 320 are angled with respect to one another at about 5 degrees or greater, although other angles are contemplated. In other words, when jaw members 310, 320 are moved apart from one another past a pre-determined threshold, e.g., an angle of about 5 degrees, piston assembly 390 has been moved to the extended position, inhibiting blade 375 from being deployed between jaw members 310, 320. Further, although piston assembly 390 may not be fully extended when jaw members 310, 320 are spaced-apart at a relatively small angle, e.g., about 5 degrees, piston assembly 390 may be configured to be sufficiently extended in this position to inhibit deployment of blade 375 into jaw members 310, 320. In other words, in this position, trigger 360 may be rotated partially (to move piston assembly 390 to the fully extended position), thereby translating blade 375 a relatively small distance distally; however, trigger assembly 380 and shaft 301a are configured such that blade 375 is still retained within shaft 301a, i.e., blade 375 does not extend into jaw members 310, 320, despite, as above, being translated a relatively small distance distally. On the other hand, when jaw members 310, 320 are spaced-apart at a relatively large angle, piston assembly 390 may be fully extended, inhibiting any substantial translation of blade 375.

Additionally, shaft member 301a and/or shaft member 301b may include a locking feature (not shown) for inhibiting piston assembly 390 from being further extended, thereby inhibiting blade 375 from being translated to the extended position, when jaw members 310, 320 are not disposed in the approximated position. In other words, the locking feature (not shown) may be configured to engage piston assembly 390 when jaw members 310, 320 are disposed between the approximated and spaced-apart positions to inhibit piston assembly 390 from being extended further. The pivotable engagement of piston assembly 390 to piston base 392 of shaft member 301b permits such a locking engagement only where jaw members 310, 320 are disposed between the approximated and spaced-apart positions since, as jaw members 310, 320 are moved to spaced-apart position (or to the approximated position), piston assembly 390 is pivoted about piston base 392 relative to shaft member 301a and/or shaft member 301b, thereby disengaging piston assembly 390 from the locking feature (not shown). Such a locking feature inhibits blade 375 from being exposed even where jaw members 310, 320 are spaced-apart a relatively small distance with respect to one another.

As shown in FIGS. 5B and 5C, and as discussed above, when jaw members 310, 320 are moved to the closed position, trigger 360 is permitted to rotate to deploy blade 375 between jaw members 310, 320 to cut tissue grasped therebetween. Thus, piston assembly 390 permits deployment of blade 375 when jaw members 310, 320 are in the approximated, or closed position, but piston assembly 390 inhibits deployment of blade 375 when jaw members 310, 320 are in the open position and returns blade 375 to the retracted position when jaw members 310, 320 are moved to the open position, to help ensure that blade 375 is not extended, or deployed between jaw members 310, 320 when jaw members 310, 320 are spaced-apart relative to one another.

Figure 6A:
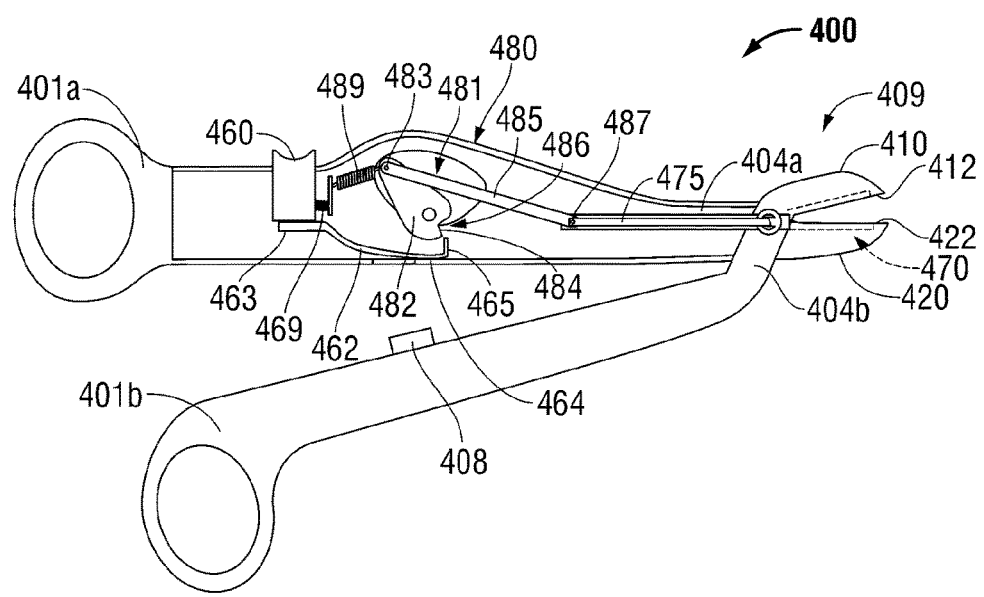
FIG. 6A is a side view of yet another embodiment of a forceps in accordance with the present disclosure shown in a first position, where a portion of a handle has been removed to show the internal components therein.
Figure 6B:
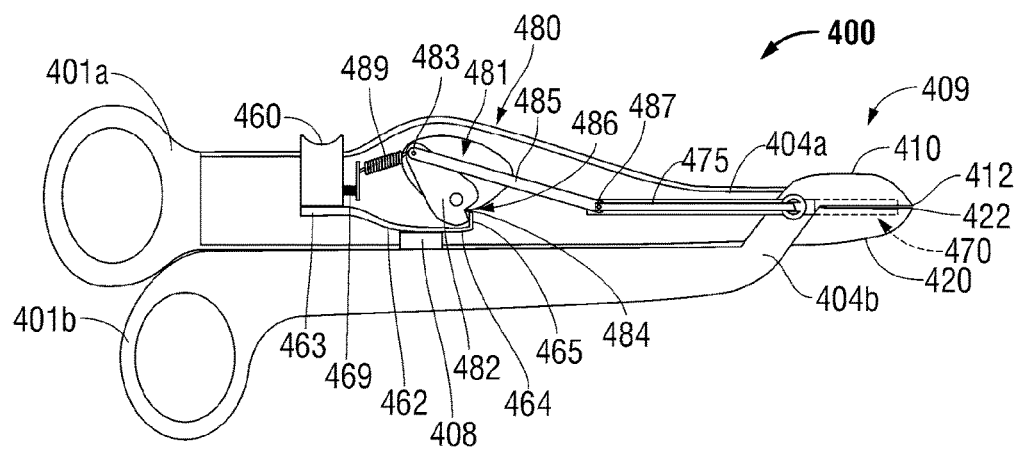
FIG. 6B is a side view of the forceps of FIG. 6A shown in a second position, where a portion of the handle has been removed to show the internal components therein.
Figure 6C:
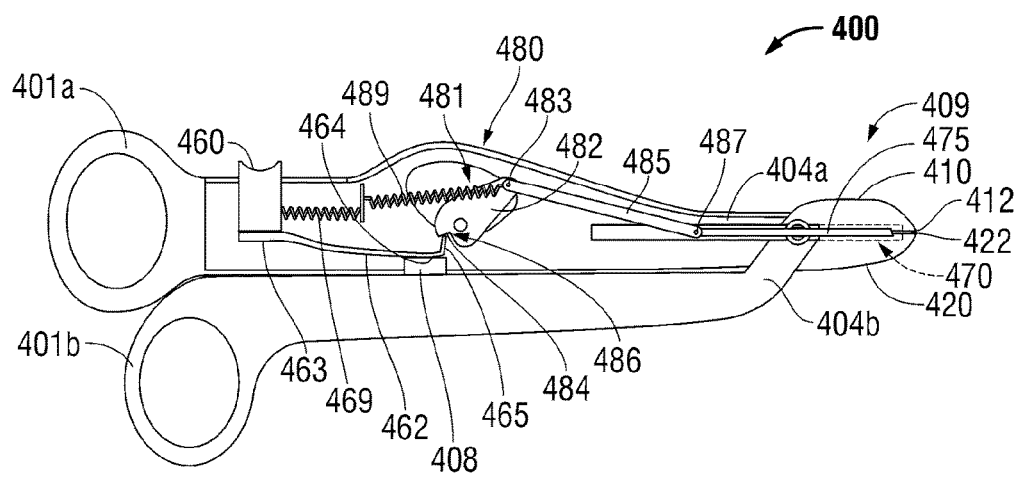
FIG. 6C is a side view of the forceps of FIG. 6A shown in a third position, where a portion of the handle has been removed to show the internal components therein.

Turning now to FIGS. 6A-6C, another embodiment of a forceps, forceps 400, is shown. Forceps 400 is similar to the previous embodiments and includes two elongated shaft members 401a, 401b having an end effector assembly 409 attached to distal ends 404a, 404b, respectively, thereof. The end effector assembly 409 includes a pair of opposing jaw members 410, 420 moveable between an open position and a closed position in accordance with movement of the shaft members 401a, 401b relative to one between a spaced-apart position and an approximated position. As in the previous embodiments, one or both of jaw members 410, 420 may include an electrically conductive sealing surface 412, 422, respectively, disposed on an opposed surface thereof for conducting electrosurgical energy through tissue to seal tissue grasped between jaw members 410, 420.

Forceps 400 also includes a trigger 460 coupled to a trigger assembly 480 disposed within one of shaft members 401a, 401b, e.g., shaft member 401a. Trigger assembly 480 is coupled to blade 475, which is selectively translatable from a retracted position, wherein blade 475 is disposed within shaft member 401a, to an extended position, wherein blade 475 extends between jaw members 410, 420, e.g., through a blade channel 470 defined within one or both of jaw members 410, 420, to cut tissue grasped between jaw members 410, 420.

With continued reference to FIGS. 6A-6C, trigger assembly 480 of forceps 400 includes a cantilever 482 pivotably mounted within shaft member 401a and disposed within a cantilever groove 481 defined within shaft member 401a. Cantilever groove 481 permits rotation of cantilever 482 between a first position (FIG. 6A) and a second position (FIG. 6C). A biasing member, e.g., spring 489 may be provided for biasing cantilever 482 toward the first position, as shown in FIG. 6A. A bar linkage 485 is coupled to first end 483 of cantilever 482 and extends distally therefrom to engage blade 475 at distal end 487 of bar linkage 485 such that, as cantilever 482 is rotated between the first position and the second position, blade 475 is translated between the retracted position and the extended position. An engagement recess 486 is defined within second end 484 of cantilever 482.

Trigger 460 extends from shaft member 401a and is selectively translatable between a distal position (FIG. 6A) and a proximal position (FIG. 6C). A biasing member, e.g., biasing spring 469, may be provided for biasing trigger 460 toward the distal position, as shown in FIG. 6A. An arm 462 is engaged to trigger 460 at proximal end 463 of arm 462 and extends distally therefrom through shaft member 401a. A finger 465 is disposed at free distal end 464 of arm 462. Finger 465 extends obliquely from arm 462 and is configured to engage engagement recess 486 defined within second end 484 of cantilever 482. As will be described in greater detail below, upon engagement of finger 465 of arm 462 and engagement recess 486 of cantilever 482, trigger 460 may be translated proximally to advance blade 475 distally to cut tissue grasped between jaw members 410, 420.

With reference now to FIG. 6A, forceps 400 is shown wherein jaw members 410, 420 and shaft members 401a, 401b are disposed in the open, or spaced-apart position. As shown in FIG. 6A, biasing spring 489 biases cantilever 482 toward the first position, while biasing spring 469 biases trigger 460 toward the distal position. Finger 465 of arm 462 is spaced-apart, or disengaged from engagement recess 486 of cantilever 482. In fact, arm 462 may be a flat spring, or other spring-like mechanism that is biased in the position shown in FIG. 6A, e.g., such that finger 465 is disengaged from engagement recess 486 of cantilever 482 when at-rest. Thus, in this spaced-apart position of jaw members 410, 420, cantilever 482 is disposed in the first position and blade 475 is disposed in the retracted position. Further, with trigger 460 disengaged from trigger assembly 480 when jaw members 410, 420 are in the open position, trigger assembly 480 is in a "safe-mode" wherein translation of trigger 460 from the distal position to the proximal position does not effect the position of blade 475, i.e., wherein trigger 460 is independent of trigger assembly 480. In other words, when trigger 460 is disengaged from trigger assembly 480, blade 475 is inhibited from being deployed.

Turning now to FIG. 6B, wherein shaft members 401a, 401b have been moved to the approximated position to move jaw members 410, 420 to the closed position, e.g., to grasp tissue therebetween. As shown in FIG. 6B, upon approximation of shaft members 401a, 401b, protrusion 408, which extends from shaft member 401b, urges arm 462 of trigger 460 toward cantilever 482 such that finger 465 of arm 462 is urged into engagement with engagement recess 486 of cantilever 482. In this position, trigger assembly 480 is "armed." However, at this point, cantilever 482 remains disposed in the first position under the bias of spring 489 such that blade 475 remains in the retracted position. Similarly, trigger 460 remains in the distal position under the bias of spring 469.

With jaw members 410, 420 disposed in the closed position grasping tissue therebetween, electrosurgical energy may be supplied to sealing surface 412 and/or sealing surface 422 of jaw members 410, 420, respectively, to seal tissue grasped therebetween. Once tissue has been sealed, blade 475 may be advanced to divide the previously sealed tissue. More particularly, when it is desired to cut tissue disposed between jaw members 410, 420, trigger 460 is translated proximally from the distal position to the proximal position against the bias of spring 469, as shown in FIG. 6C. As trigger 460 is translated proximally, arm 462 and finger 465 are likewise pulled proximally. Accordingly, since finger 465 of arm 462 is engaged within engagement recess 486 of cantilever 482, proximal pulling of finger 465 effects rotation of cantilever 482 within cantilever groove 481 from the first position to the second position, against the bias of spring 489. As cantilever 482 is rotated to the second position, bar linkage 485 is translated distally and, in turn, blade 475 is advanced distally from shaft 401a into blade channel 470 defined within jaw member 420 to cut tissue grasped between jaw members 410, 420.

Once blade 475 has been deployed to the extended position, e.g., between jaw members 410, 420 to cut tissue therebetween, trigger 460 may be released, allowing trigger 460 to return to the distal position under the bias of spring 469 and allowing cantilever 482 to return to the first position under the bias of spring 489 such that blade 475 is returned to the retracted position.

Engagement groove 486 of cantilever 482 may be configured such that, upon rotation of cantilever 482 to the second position (wherein blade 475 is translated to the extended position), finger 485 is released from engagement groove 486, or falls out of engagement with engagement groove 486, allowing cantilever 482 and, thus, blade 475, to return to the first, or retracted position under the bias of spring 489 (regardless of the relative position of trigger 460). Alternatively, or additionally, once blade 475 has been deployed to the extended position to cut tissue disposed between jaw members 410, 420, the user may move shaft members 401a, 401b to the spaced-apart position to move jaw members 410, 420 to the open position. As shaft members 401a, 401b are moved to the spaced-apart position, protrusion 408 extending from shaft member 401b is moved apart from arm 462, allowing arm 462 to return to its biased, or at-rest position, spaced-apart from cantilever 482. Accordingly, upon movement of shaft members 401a, 401b to the open position, arm 462 is disengaged from engagement groove 486 of cantilever 482, allowing cantilever 482 and, thus, blade 475 to return to the first, or retracted position under the bias of spring 489. With forceps 400 disposed in the open position, and with blade 475 retracted within shaft 401a, forceps 400 may be removed from the surgical site.

Figure 7A:
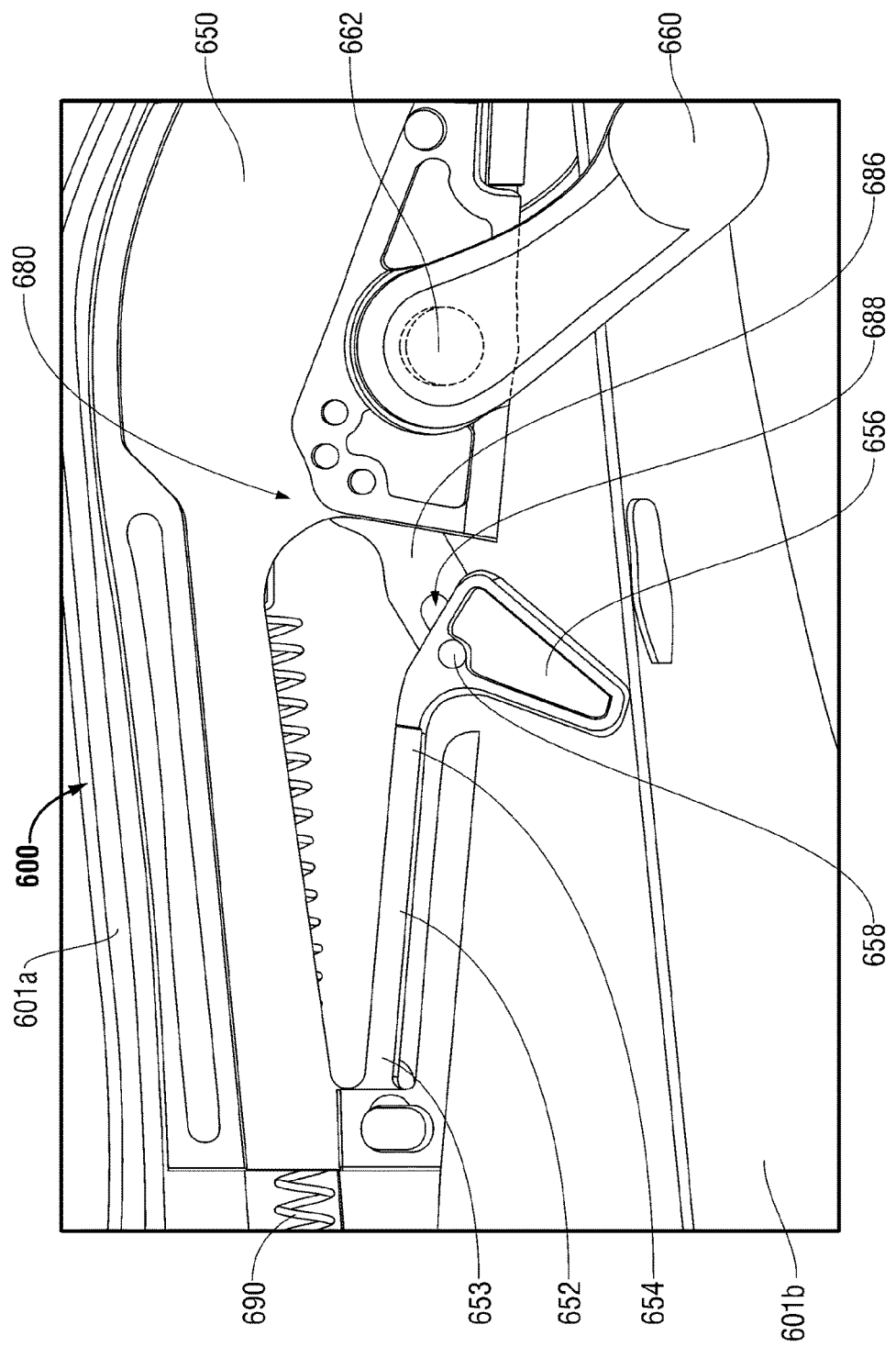
FIG. 7A is a side view of still yet another embodiment of a forceps in accordance with the present disclosure shown in a first position, wherein a portion of the handle has been removed to show the internal components therein.
Figure 7B:
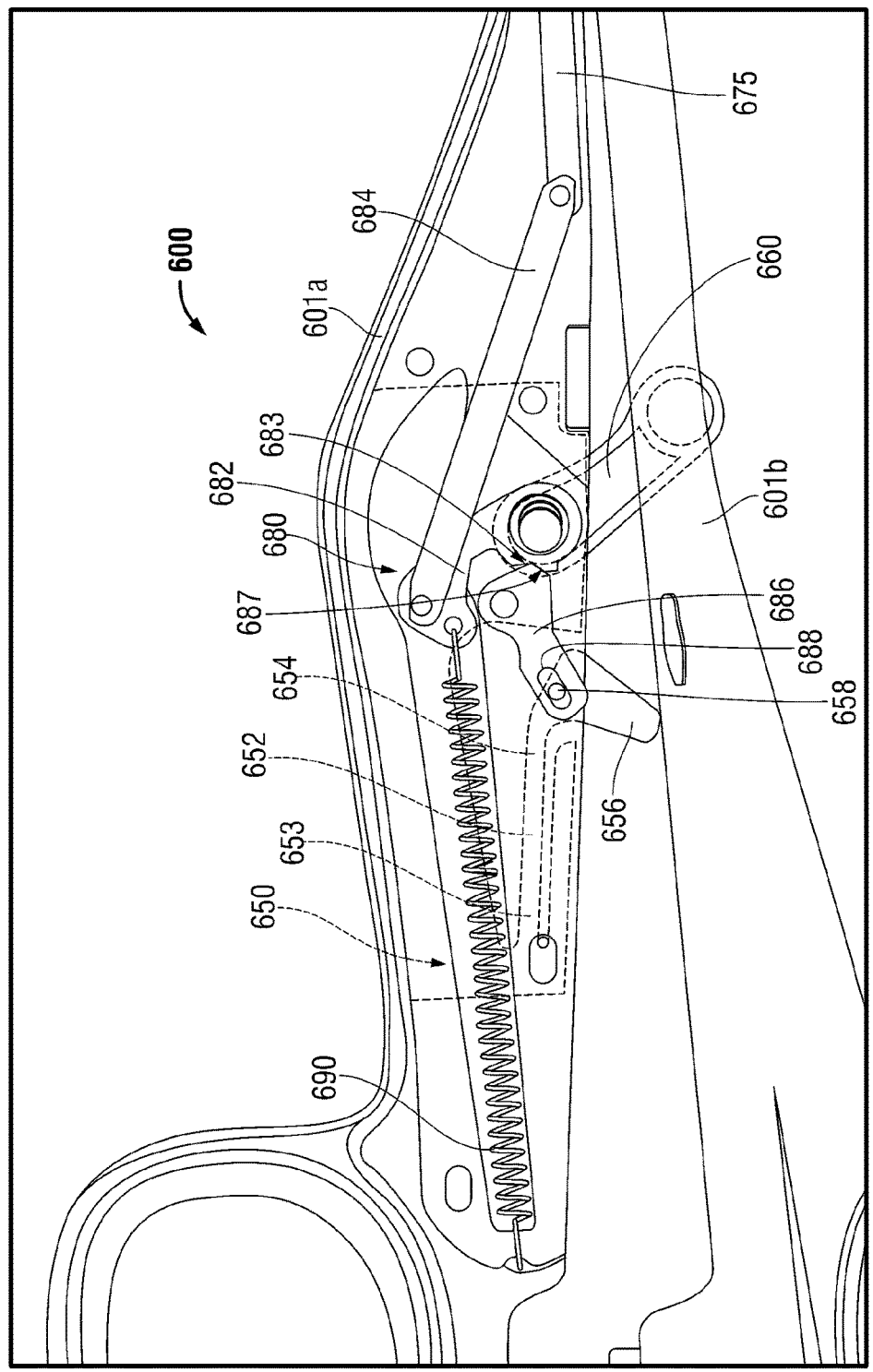
FIG. 7B is a side view of the forceps of FIG. 7A shown in the first position, wherein a portion of a cover plate has been removed to further show the components therein.
Figure 7C:
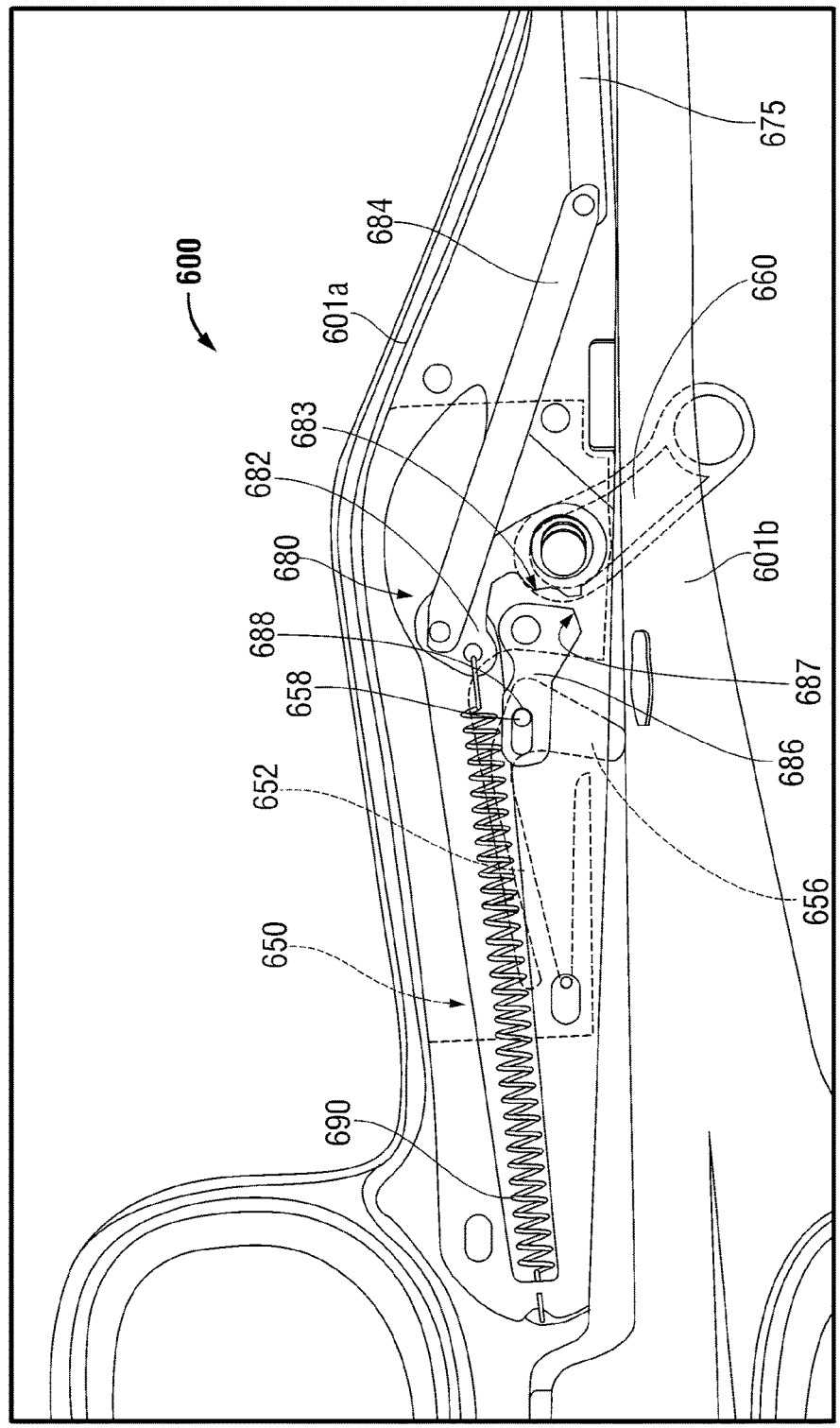
FIG. 7C is a side view of the forceps of FIG. 7A shown in a second position wherein a portion of a cover plate has been removed to further show the components therein.

With reference now to FIGS. 7A-7C, another embodiment of a forceps 600, similar to forceps 100 (FIG. 1), is shown. Forceps 600 includes first and second shaft members 601a, 601b, respectively, configured to engage an end effector assembly, e.g., end effector assembly 109 (FIG. 1), at the distal ends thereof. As in the previous embodiments, shaft members 601a, 601b are moveable relative to one another to move jaw members 110, 120 (FIG. 1) of end effector assembly 109 (FIG. 1) between a spaced-apart position and an approximated position for grasping and/or sealing tissue. Forceps 600 further includes a trigger 660 coupled to a trigger assembly 680 for selectively advancing a blade 675 (FIG. 7B) between jaw members 110, 120 (FIG. 1) for dividing tissue grasped therebetween.

Trigger assembly 680 is similar to trigger assembly 180 of forceps 100 (see FIGS. 3A-3C) and generally includes a pivoting linkage 682, a bar linkage 684, an interference member 686, and a biasing spring 690. However, trigger assembly 680 differs from trigger assembly 180 (FIGS. 3A-3C) in that trigger assembly 680 further includes a cover plate 650 positioned within shaft member 601a, as best shown in FIG. 7A. Cover plate 650 is engaged to shaft member 601a and anchors the pivot pins (not explicitly shown) of trigger 660, pivoting linkage 682, and interference member 686, allowing trigger 660, pivoting linkage 682, and interference member 686 to rotate relative to shaft member 601a and cover plate 650. Cover plate 650 further includes a proximal portion including a leaf spring 652 (or other biasing member) extending distally therefrom. Leaf spring 652 is engaged to cover plate 650 at a proximal end 653 thereof and includes a protrusion 656 disposed at a distal end 654 thereof. Leaf spring 652 biases protrusion 656 to extend from shaft member 601a toward shaft member 601b, as shown in FIGS. 7A and 7B. In this position, pin 658, which is fixedly engaged to protrusion 656, is disposed at a proximal end of slot 688 defined within interference member 686. Although protrusion 656 is shown engaged to leaf spring 652 of cover plate 650, protrusion 656 may alternatively be disposed on shaft member 601b.

Turning now to FIG. 7B, wherein a distal portion of cover plate 650 has been removed to show the underlying components of trigger assembly 680. As shown in FIG. 7B, shaft members 601a, 601b are spaced-apart from one another, corresponding to the spaced-apart position of jaw members 110, 120 of end effector assembly 109 (FIG. 1). In this position, protrusion 656 is biased by leaf spring 652 toward its at-rest position (extending from shaft member 601a toward shaft member 601b). With protrusion 656 biased toward its at-rest position, as mentioned above, pin 658 is retained in position at the proximal end of slot 688 defined within interference member 686 such that interference member 686 is rotatably fixed in engagement with pivoting linkage 682. More specifically, protrusion 656, when disposed in the at-rest position, maintains interference member 686 in position such that distal engaging surface 687 of interference member 686 is engaged with proximal engaging surface 683 of pivoting linkage 682, inhibiting rotation of pivoting linkage 682. Accordingly, with interference member 686 inhibiting rotation of pivoting linkage 682, trigger 660 is inhibited from being rotated and blade 675 is inhibited from being deployed. In other words, when shaft members 601a, 601b are spaced-apart from one another and, thus, when jaw members 110, 120 (FIG. 1) are disposed in the spaced-apart position, blade 675 is inhibited from being deployed.

Turning now to FIG. 7C, upon approximation of shaft members 601a, 601b, e.g., upon moving of jaw members 110, 120 (FIG. 1) toward the approximated position, shaft member 601b eventually contacts protrusion 656, which initially extends from shaft member 601a toward shaft member 601b. As shaft members 601a, 601b are further approximated relative to one another, shaft member 601b urges protrusion 656 upwardly back into shaft member 601a. More specifically, as shaft member 601b contacts protrusion 656, leaf spring 652 is deflected from its at-rest position and protrusion 656 is moved, against the bias of leaf spring 652, upwardly into shaft member 601b. As protrusion 656 is translated upwardly into shaft member 601b, interference member 686 is rotated in a clockwise direction due to the engagement of pin 658 of protrusion 656 within slot 688 of interference member 686. At the same time, pin 658 is translated along slot 688 to the distal end thereof. As a result of this upward movement of protrusion 656, interference member 686 and, thus distal engaging surface 687 of interference member 686 are rotated clockwise such that distal engaging surface 687 of interference member 686 is disengaged from proximal engaging surface 683 of pivoting linkage 682, as shown in FIG. 7C. In this position, pivoting linkage 682 is no longer inhibited from rotating and, thus, trigger 660 may be actuated to rotate pivoting linkage 682 to advances bar linkage 684 distally. As bar linkage 684 is advanced distally, blade 675 (FIG. 7B) is translated distally from shaft 601b and between jaw members 110, 120 (FIG. 1) to divide tissue grasped therebetween.

Upon release of trigger 660, blade 675 is automatically retracted proximally back into shaft member 601a under the bias of biasing spring 690. Thereafter, jaw members 110, 120 (FIG. 1) may be moved to the spaced-apart position and forceps 600 may be withdrawn from the surgical site. As shaft members 601a, 601b are moved apart from one another, e.g., to move jaw members 110, 120 (FIG. 1) to the spaced-apart position, shaft 601b is moved apart from protrusion 656, allowing protrusion 656 to return to its at-rest position under the bias of leaf spring 652. The return of protrusion 656 to the at-rest position urges pivot pin 658 downwardly and proximally along slot 688 and relative to interference member 686 such that interference member 868 is rotated counterclockwise. This counterclockwise rotation of interference member 686 effects similar rotation of distal engaging surface 687 of interference member 868 such that distal engaging surface 687 is rotated back into engagement with proximal engaging surface 683 of pivoting linkage 682 to lock trigger assembly 680 and prevent deployment of blade 675. Put more generally, trigger assembly 680 inhibits blade 675 from being deployed when jaw members 110, 120 (FIG. 1) are disposed in the spaced-apart position and permits deployment of blade 675 when jaw members 110, 120 (FIG. 1) are moved to the approximated position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    a first shaft member having a jaw member at a distal end thereof;
    a second shaft member having a jaw member at a distal end thereof;
    the first and second shaft members pivotally coupled to each other about a pivot to move the jaw members between an open position and a closed position;
    a trigger disposed on one of the first or second shaft members;
    a blade operatively coupled to the trigger such that actuation of the trigger translates the blade;
    an interference member engaged with the trigger when the jaw members are in the open position to prevent actuation of the trigger, one of the first or second shaft members configured to contact the interference member to move the interference member out of engagement with the trigger when the jaw members are moved to the closed position to permit actuation of the trigger;
    an actuator disposed within a recess formed in the first shaft member such that the actuator is recessed from an outer surface of the first shaft member, the actuator configured to supply electrosurgical energy to at least one of the jaw members; and a tab extending from the second shaft member and configured to be received within the recess upon approximation of the first and second shaft members to depress the actuator.

2. The forceps according to claim 1, wherein each of the first and second shaft members includes a handle disposed at a proximal end thereof, each of the handles defining a finger hole to facilitate movement of the jaw members between the open and closed positions.

3. The forceps according to claim 1, wherein at least one of the jaw members includes a blade channel extending at least partially therethrough and configured to receive the blade upon distal translation of the blade.

4. The forceps according to claim 1, wherein at least one of the jaw members includes an electrically conductive sealing surface adapted to electrically connect to a source of electrosurgical energy.

5. The forceps according to claim 1, wherein depression of the actuator maintains a supply of electrosurgical energy to at least one of the jaw members for a fixed length of time.

6. The forceps according to claim 1, wherein depression of the actuator maintains a continuous supply of electrosurgical energy to at least one of the jaw members.

7. The forceps according to claim 1, wherein the actuator is an electrical toggle switch.

8. The forceps according to claim 1, wherein the recess is disposed proximal to the trigger.

9. The forceps according to claim 1, wherein the recess defines an opening through the outer surface of the first shaft member, the tab configured to extend through the opening to be received within the recess to depress the actuator upon approximation of the first and second shaft members.

10. A forceps, comprising:
a first shaft member having a jaw member at a distal end thereof;
a second shaft member having a jaw member at a distal end thereof,
the first and second shaft members pivotally coupled to each other about a pivot to move the jaw members between an open position and a closed position;
a trigger disposed on one of the first or second shaft members;
a blade operatively coupled to the trigger such that actuation of the trigger translates the blade;
an interference member engaged with the trigger when the jaw members are in the open position to prevent actuation of the trigger, one of the first or second shaft members configured to contact the interference member to move the interference member out of engagement with the trigger when the jaw members are moved to the closed position to permit actuation of the trigger;
an actuator disposed within a recess formed in the first shaft member, the actuator configured to supply electrosurgical energy to at least one of the jaw members; and
a tab extending from the second shaft member toward the first shaft member and configured to be received within the recess upon approximation of the first and second shaft members to depress the actuator.

11. The forceps according to claim 10, wherein each of the first and second shaft members includes a handle disposed at a proximal end thereof, each of the handles defining a finger hole to facilitate movement of the jaw members between the open and closed positions.

12. The forceps according to claim 10, wherein at least one of the jaw members includes a blade channel extending at least partially therethrough and configured to receive the blade upon distal translation of the blade.

13. The forceps according to claim 10, wherein at least one of the jaw members includes an electrically conductive sealing surface adapted to electrically connect to a source of electrosurgical energy.

14. The forceps according to claim 10, wherein depression of the actuator maintains a supply of electrosurgical energy to at least one of the jaw members for a fixed length of time.

15. The forceps according to claim 10, wherein depression of the actuator maintains a continuous supply of electrosurgical energy to at least one of the jaw members.

16. The forceps according to claim 10, wherein the actuator is an electrical toggle switch.

17. The forceps according to claim 10, wherein the recess is disposed proximal to the trigger.

18. The forceps according to claim 10, wherein the actuator is recessed from an outer surface of the first shaft member.

19. The forceps according to claim 10, wherein the recess defines an opening through an outer surface of the first shaft member, the tab configured to extend through the opening to be received within the recess to depress the actuator upon approximation of the first and second shaft members.

* * * * *